(12) United States Patent
Xie et al.

(10) Patent No.: US 9,381,328 B2
(45) Date of Patent: Jul. 5, 2016

(54) BALLOON SYSTEM FOR TREATING SINUSITIS OR ALLERGIC RHINITIS

(71) Applicant: PUYI (SHANGHAI) BIOTECHNOLOGY CO., LTD., Pudong, Shanghai (CN)

(72) Inventors: Jian Xie, Shanghai (CN); Zheng Wei, Shanghai (CN)

(73) Assignee: PUYI (Shanghai) Biotechnology Co., Ltd., Shanghai (CN)

( * ) Notice: Subject to any disclaimer, the term of this patent is extended or adjusted under 35 U.S.C. 154(b) by 0 days.

(21) Appl. No.: 14/401,210

(22) PCT Filed: Sep. 23, 2013

(86) PCT No.: PCT/CN2013/083982
§ 371 (c)(1),
(2) Date: Nov. 14, 2014

(87) PCT Pub. No.: WO2014/075513
PCT Pub. Date: May 22, 2014

(65) Prior Publication Data
US 2015/0265813 A1   Sep. 24, 2015

(30) Foreign Application Priority Data

Nov. 13, 2012   (CN) .......................... 2012 1 0454915

(51) Int. Cl.
*A61M 29/00* (2006.01)
*A61M 25/10* (2013.01)
(Continued)

(52) U.S. Cl.
CPC ............ *A61M 25/1034* (2013.01); *A61B 17/24* (2013.01); *A61M 25/1006* (2013.01);
(Continued)

(58) Field of Classification Search
CPC ............... A61M 25/1034; A61M 25/1006; A61M 2025/1075; A61M 25/1025; A61M 2025/1054; A61M 2025/1031; A61M 2025/1061; A61M 31/002; A61M 29/02; A61M 2210/0681; A61J 15/003; A61J 15/0049; A61J 15/0053
See application file for complete search history.

(56) References Cited

U.S. PATENT DOCUMENTS

| 6,364,856 B1 * | 4/2002 | Ding .......................... A61F 2/86 427/2.1 |
| 2006/0085028 A1 * | 4/2006 | Boock ................... A61M 25/10 606/200 |

(Continued)

FOREIGN PATENT DOCUMENTS

| CN | 201676386 U | 12/2010 |
| CN | 201743734 U | 2/2011 |

(Continued)

OTHER PUBLICATIONS

Fixed Definition,2015 , Merriam-Webster Incorporated.*
(Continued)

*Primary Examiner* — Laura Bouchelle
*Assistant Examiner* — Morgan Lee
(74) *Attorney, Agent, or Firm* — Dickinson Wright PLLC

(57) ABSTRACT

A balloon system for treating sinusitis or allergic rhinitis includes a central inner tube, a balloon to be filled and a balloon catheter outer tube, all of which axially extend. The central inner tube includes a distal end part and a proximal end part detachably connected with each other by a connector in an axial direction. A first end of the balloon is connected to the distal end part, and a second end of the balloon and the balloon catheter outer tube are detachably connected with each other by the connector. The balloon catheter outer tube is radially outwardly spaced from the proximal end part, and the connector includes a first grommet and a second grommet rotating coaxially and relatively fixed with each other in axial direction. Each of the first grommet and second grommet has at least one gas port.

20 Claims, 8 Drawing Sheets

(51) Int. Cl.
*A61B 17/24* (2006.01)
*A61F 2/18* (2006.01)

(52) U.S. Cl.
CPC .......... *A61F 2/18* (2013.01); *A61F 2220/0033* (2013.01); *A61F 2250/0003* (2013.01); *A61F 2250/0068* (2013.01); *A61M 2210/0681* (2013.01)

(56) References Cited

U.S. PATENT DOCUMENTS

2007/0088380 A1* 4/2007 Hirszowicz ....... A61M 25/1006 606/194

| | | |
|---|---|---|
| 2007/0276314 A1 | 11/2007 | Becker |
| 2010/0312101 A1 | 12/2010 | Drontle et al. |
| 2011/0160740 A1 | 6/2011 | Makower et al. |

FOREIGN PATENT DOCUMENTS

| | | |
|---|---|---|
| CN | 102125719 A | 7/2011 |
| CN | 102500042 A | 6/2012 |
| CN | 103007425 A | 4/2013 |
| WO | 2012030668 A1 | 3/2012 |

OTHER PUBLICATIONS

Detach Definition,2015, Merriam-Webster Incorporated.*
International Search Report Dated Jan. 2, 2014, Eight (8) Pages.

* cited by examiner

BALLOON SYSTEM FOR TREATING SINUSITIS OR ALLERGIC RHINITIS

CROSS REFERENCE TO RELATED APPLICATION

This U.S. National Stage Patent Application claims the benefit of International Application Serial No. PCT/CN2013/083982 filed on Sep. 23, 2013, the entire disclosure of which is incorporated herein by reference.

BACKGROUND OF THE INVENTION

1. Field of the invention

This invention relates generally to medical devices, and more particularly to a balloon system for treating sinusitis or allergic rhinitis.

2. Related art

Sinusitis is a common Ear-Nose-Throat (ENT) disease for the person between 5 and 79 years old. Its incidence takes 15 percent of the population with trend toward gradual increase. Sinus is aerated cavities of the facial bone around the nasal cavity. The inflammation of the sinus causes the expansion of locations of pathological changes, which blocks the pathway for the nasal air and nasal mucus, and results in nasal mucus countercurrent, build up pressure and thus cause headache. In addition to headache, typical symptoms of acute sinusitis include nasal congestion, thick nasal mucus, temporary olfactory dysfunction, chills, fever, inappetence, constipation, general malaise and so on. Children and infants may have the symptoms including vomiting, diarrhea, coughing and so on. The thick nasal mucus may irritate the throat, and result in throat problem such as pharyngolaryngitis and so on. Intense acute sinusitis may result in ophthalmic infections. However, the complication of acute sinusitis, such as orbital infections, rarely occurs due to the wide application of antibiotic in recent years.

The functional nasal endoscopic surgical procedure (FESS) is effective for the acute sinusitis and chronic sinusitis. Tissue and bone with pathological changes can be removed precisely to expand the ostium of the sinus and to restore the normal physiological function of the sinus. The nasal endoscopic surgical procedure is minimally invasive compared with the traditional sinusitis surgery.

However, nasal endoscopic surgical procedure is expensive and not thorough. The resulted relapse will cause the repeated treatment, which costs a lot and brings heavy mental and economic burdens to patients.

Allergic rhinitis, also known as nasal allergies, is an upper respiratory disease with complicated pathogeny. The allergic rhinitis caused by pollen allergy is also called pollenosis, hay fever, or seasonal allergic rhinitis.

Usually, once the patient contacts with or inhales allergens, the IgE (immunoglobulin E) in vivo will cause the mast cells to release histamine and thus cause allergic reactions. Allergens are the antigens inducing and reacting with specific IgE antibody. Most allergens are derived from animals, plants, insects, fungus or other specific substances. Allergens can be divided into inhalational allergens and alimentary allergens. The inhalational allergen is the main reason of allergic rhinitis. Symptoms of allergic rhinitis mainly include telangiectasis, increased permeability, increased glandular secretion, and eosinophilic infiltration, etc. Proliferative changes in the mucosa epithelium, mucosal hypertrophy and polypoid lesion will be resulted if above symptoms are recurrent. It has flu-like symptoms, which primarily include nasal itching, nasal congestion, snot, sneezing and watery rhinorrhea (ninny nose), etc. These symptoms are intermittent and recurrent with pale edema of nasal mucosa. The worse will evolve into sinusitis, asthma or ear infections.

Drug therapies don't have positive effect for allergic rhinitis. Surgical therapies for allergic rhinitis mainly comprise nerve block surgery, low-temperature plasma surgery, inferior turbinate mucosa surgery, parasympathetic-excitability-decreasing surgery and so on. However, both the recurrence rate and cost of these surgeries are high.

In addition, special medical instruments, such as a nasal irrigator, have been developed to treat refractory nasal disease such as sinusitis. CN202314874U discloses a sinusitis therapy tube for cleaning the nasal cavity, wherein, injected liquid medicine is used to irrigate and immerse the nasal cavity, and then the pus is discharged via a discharging pipe. As compared with ordinary nasal spray, the invention can clean the nasal cavity better, which is beneficial for the patient to recover from inflammation. However, the disadvantage of these irrigators is that the nasal sinus ostium of the patient is narrow or even blocked, thus the liquid medicine can be irrigated only to the turbinate rather than to the interior of the frontal sinus and maxillary sinus, however, the interior of the nasal sinus is just the source of the inflammation. Actually, even if the liquid medicine can be irrigated to the interior of the nasal cavity, the brief contact with medicine can only alleviate the inflammation, and after the effect of the medicine disappears the narrow nasal sinus ostium causes the interior of the nasal cavity back to the status before the irrigation. Therefore, nasal irrigation is only used as an adjunctive therapy rather than a dominant technology during nasal cavity surgery or treatment.

CN201676386U discloses a balloon catheter for treating rhinitis and sinusitis, which is developed from cardiovascular dilation technology. All parts of the catheter (i.e. the first, second and third connector parts) are permanently connected with one another in structure, to form a whole which cannot be disassembled freely. This kind of catheter therapy technology based on cardiovascular disease treatment has been applied to nasal sinus open surgery by American engineers in 2002, and certificated by FDA in 2005, and finally approved for clinical application. The application of the balloon catheter disclosed in the patent is similar to PTCA technology (Percutaneous Transluminal Coronary Angioplasty), namely, with the euthyphoria in nasal endoscopy, an uninflated pressure-endurable balloon is disposed in the sinus ostium to be opened, then the balloon is inflated for a period of time, thus the balloon will press and expand the sinus ostium, so that the inelastic bone structure fractures and expands, and the elastic mucosa tissue is pressed and deformed, consequently the sinus ostium is expanded and smooth and continuous airway is obtained. Nowadays, PTCA technology application in tubular artery operation decreases year by year, for the reason that the narrow part of the blood vessel temporarily expanded by the balloon is easy to narrow even close again. The similar situation can also happen to balloon Sinuplasty technology, that is to say, although the balloon catheter disclosed by CN201676386U is convenient and efficient, after the balloon is removed, the expanded passage is easy to be blocked once again due to the patients' pathological regeneration or tissue recoil, thus the therapy in the patient cannot provide sufficient time for treating the diseases such as sinusitis until complete cure.

US20070250105A1 discloses a device and method for treatment of sinusitis, which refers to an expanded balloon delivered into the maxillary sinus ostium through nasal cavity or maxillary sinus puncture for supporting the sinus ostium. All parts of the balloon system including the balloon are permanently connected with one another and cannot be disassembled freely, therefore, the balloon system is entirely taken out after expanding the maxillary sinus ostium. The disadvantage of ordinary balloon sinuplasty technology is referred to in CN201676386U and not described here. US20070250105A1 further refers to a support (such as coronary stent) implanted into the sinus ostium, wherein the support is independent from the balloon system and used to maintain the sinus ostium unblocked. However, as the structure of the nasal cavity is different from that of the coronary, and the nasal cavity has complex structure with individual difference, ordinary supports may not be adequate for the nasal cavity structure, and the implanted support increases the cost of the surgery and patient's burden.

Consequently, the expanded airway must be maintained for enough time, and medicines should be continuously provided under this condition, such that the diseased region can be cured radically and tissue function can be recovered, thus the possibility of recurrence of airway blockage is minimized and the surgery wound and cost are decreased as much as possible.

SUMMARY OF THE INVENTION

The purpose of the invention is to provide a balloon system for treating sinusitis or allergic rhinitis so as to overcome the problem in the prior art that after the balloon is taken out, the expanded airway is blocked again.

For above purpose, the invention provides a balloon system for treating sinusitis or allergic rhinitis, comprising a central inner tube, a balloon to be filled and a balloon catheter outer tube, all of which axially extend; the central inner tube including a distal end part and a proximal end part detachably connected with each other by a connector in axial direction; a first end of the balloon is connected to the distal end part, and a second end of the balloon and the balloon catheter outer tube are detachably connected with each other by the connector; the balloon catheter outer tube is radially outwardly spaced from the proximal end part, the connector includes a first grommet and a second grommet rotating coaxially and relatively fixed with each other in axial direction, each of the first grommet and second grommet has at least one gas port.

The unfilled balloon has both radial and axial lengths of 0.5 mm to 5 mm, and the filled balloon has a radial diameter of 2 mm to 30 mm and an axial length of 5 mm to 60 mm.

The filled balloon has a cylindrical shape, a dumb-bell shape or a bi-conical shape.

The balloon is made of degradable materials or non-degradable materials.

The balloon made of non-degradable materials is removed in 15 to 30 days after implantation.

The degradation period of the balloon made of degradable materials is 15 days to 9 months.

The balloon is made of copolymers including water-soluble materials.

The outer surface of the balloon includes a medicine sustained release coating.

The medicine release time of the medicine sustained release coating is 7 days to 6 months.

The balloon and the distal end part define an expanding inner cavity for containing an expanding medium which includes medicine molecules.

The connector includes a first grommet and a second grommet rotating coaxially and relatively fixed with each other in axial direction, each of the first grommet and second grommet has at least one gas port.

An outer edge of the first grommet and the balloon are permanently connected; an outer edge of the second grommet and the balloon catheter outer tube are detachably connected; an inner edge of the first grommet and the distal end part are permanently connected; an inner edge of the second grommet and the proximal end part are detachably connected; a first snap is disposed on the first grommet, and a second snap is disposed on the second grommet and interlocked with the first snap.

When the first snap is interlocked with the second snap, the first gas port of the first grommet and the second gas port of the second grommet are completely misaligned with each other.

The first snap projects axially from the first grommet towards the second grommet, and the second snap projects axially from the second grommet towards the first grommet.

The axial extending length of the second snap inside the second grommet is ⅓ to ¾ of the thickness of the second grommet.

The balloon may be a compliant balloon or half-compliant balloon, which is preferably folded as a minimal outer profile before coming into the nasal cavity, so as to go through the gap of the nasal cavity and reach the diseased region. The filled balloon may have a cylindrical shape, and further may have a dumb-bell shape or a bi-conical shape after expansion, preferably a dumb-bell shape. Both ends of the balloon have a larger diameter for remaining in the nasal cavity after expansion, thus the position of the balloon will not change freely in short-term or long-term after implantation. Preferably, the filled balloon has a radial diameter of 2 mm to 30 mm and an axial length of 5 mm to 60 mm, and the unfilled balloon has both radial and axial lengths of 0.5 mm to 5 mm.

The balloon of the balloon system for treating sinusitis or allergic rhinitis of the invention can be made of degradable materials or non-degradable materials. The non-degradable balloon can be removed in 15 to 30 days after implantation, and the degradable balloon will be degraded and absorbed as time goes on, with the preferred degradation period being 15 days to 9 months. The materials of the balloon include but are not limited to non-degradable materials such as polyamide, polyamide-polyether block copolymer, polytetrafluoroethylene, polyurethane, vinylsiloxane rubber, natural rubber, butadiene-acrylonitrile rubber; degradable materials, such as polylactic acid, L-polylactic acid, polyglycolic acid/ polylactic acid copolymer, polycaprolactone, polyhydroxybutyrate-hydroxyvalerate, polyacetylglutamic acid, polyorthodester, polyoxyethylene/polybutylene copolymer and so on.

Furthermore, the materials of the balloon may be a mixture of two or more polymers, one or more of which is a fast-degradable or water-soluble polymer. These kinds of materials (fast-degradable or water-soluble polymer) may be softened or dissolved in one or several days. When the balloon expands the nasal sinus tissue, the inside of the balloon is full filled with medicine liquid. As the fast-degradable or water-soluble polymer is continually dissolved out from the balloon materials, the medicine liquid in the balloon will gradually permeate into the diseased region through the wall of the balloon. The medicine may be the same as the medicine applied on the surface of the balloon, or different from the medicine applied for later stage of treatment. After medicine permeation is finished, the rest of the balloon can be taken out from the nasal cavity. The key of the solution is that the inner tube of the balloon must be made of materials with relatively better rigidity, such that the balloon will not be crashed even if the supporting pressure for the balloon disappears.

Typical water-soluble polymers include polyethylene glycol (PEG), polyethylene glycol block copolymer (such as PEG/PLGA, PEG/PLA bi-block or tri-block copolymer, or PEG/PLGA, PEG/PLA bi-block or tri-block random copolymer or alternating copolymer, which includes polyethylene glycol as the end of macromolecular chain), sucrose, starch, sodium alginate, polyvinylpyrrolidone (PVP), polyvinyl alcohol (PVA) and so on.

Furthermore, an outer surface of the balloon of the balloon system for treating sinusitis or allergic rhinitis of the invention can include a medicine sustained release coating, and the coating with pre-prepared medicine liquid may be applied on the outer surface of the balloon by dipping, painting, spraying, sputtering and so on. After implantation, the medicine inside the coating on the surface of the balloon releases continually for treating the diseased region around. According to the balloon implantation time and disease requirement, the medicine release time may be controlled in 7 days to 6 months.

In the above medicine coating, available medicines include but are not limited to the following medicines and their composition and/or mixture: long-acting sterol hormone, anti-inflammatory drug, anti-allergic reaction drug, parasympathicolytic drug, anti-histamine drug, anti-infectious drug, anti-platelet drug, anti-coagulant drug, anti-thrombotic drug, anti-scar drug, anti-hyperplasia drug, chemotherapeutic drug, anti-neoplastic drug, decongestant, healing accelerator, vitamin (such as retinoic acid, vitamin A, vitamin B, and their derivatives), immunomodulating agent, immunosuppressive drug.

By the means of the detachably connected distal end part and proximal end part, and the detachably connected balloon and balloon catheter outer tube, the filled balloon remains in the diseased region of the patient for short-term or long-term temporal support. Both ends of the balloon have a larger diameter for remaining in the nasal cavity after expansion, thus the position of the balloon will not change freely in the short-term or long-term after implantation. The outer surface of the balloon is coated with medicine to provide drug therapy for the diseased region. According to the above solutions, the balloon system for treating sinusitis or allergic rhinitis of the invention can be used to deliver the medicine according to the prescribed dosage during and/or after minimally invasive surgery, and also can be used after sinus atherectomy or used directly without sinus atherectomy.

DETAILED DESCRIPTION OF THE PREFERRED EMBODIMENTS

The features and advantages of the balloon system for treating sinusitis or allergic rhinitis in the present invention will become more readily appreciated when considered in connection with the following detailed description, preferred embodiments and appended drawings.

In this text, the term "proximal end" hereafter refers to an end near to the operator, namely the end close to the balloon catheter receptacle; the term "distal end" hereafter refers to an end far away from the operator, namely the end close to the diseased region.

Figure 1:
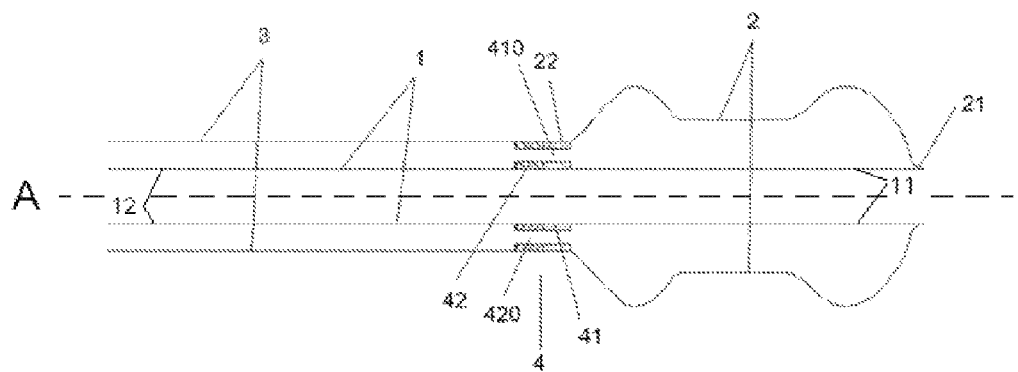
FIG. 1 is the section view of the balloon system for treating sinusitis or allergic rhinitis with the connector in unmatched status according to one preferred embodiment of the invention.
Figure 2:
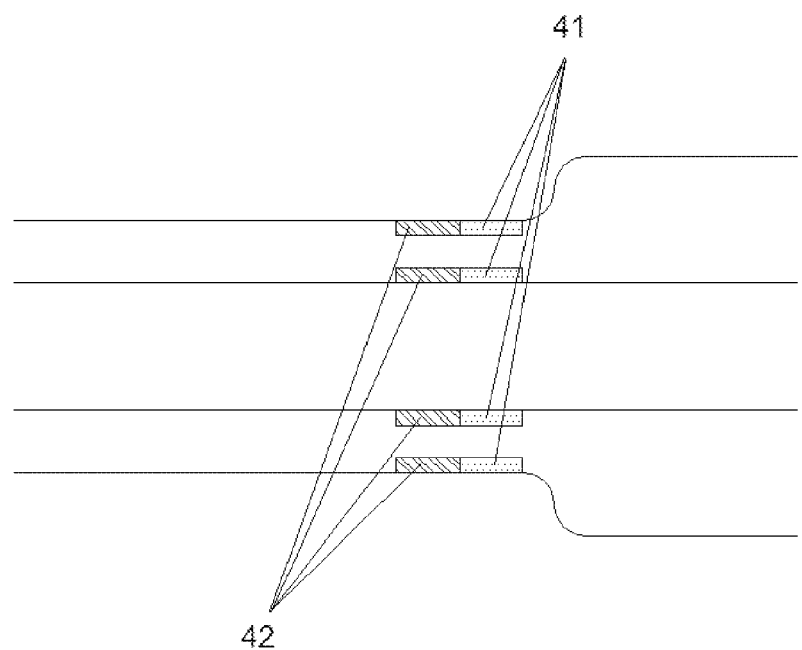
FIG. 2 is the partial section view of the balloon system for treating sinusitis or allergic rhinitis with the connector in unmatched status according to one preferred embodiment of the invention.
Figure 3:
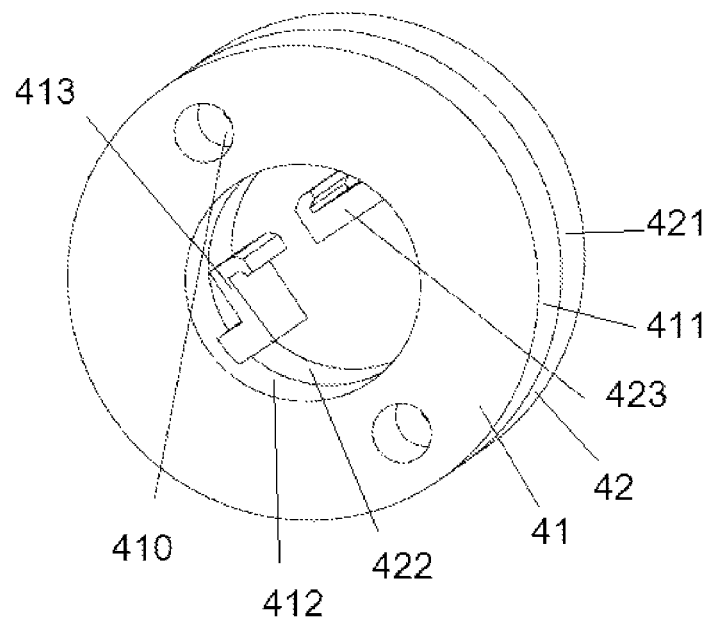
FIG. 3 is the perspective view of the connector of the balloon system for treating sinusitis or allergic rhinitis in unmatched status according to one preferred embodiment of the invention.
Figure 4:
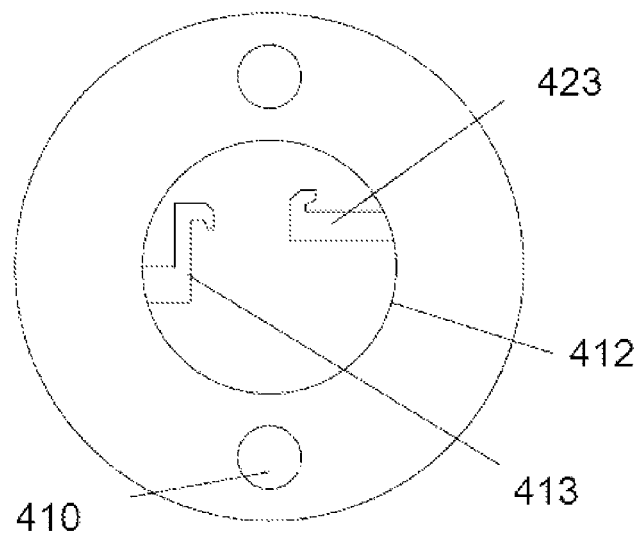
FIG. 4 is the side view of the connector of the balloon system for treating sinusitis or allergic rhinitis in unmatched status according to one preferred embodiment of the invention.

As shown in FIG. 1, the balloon system for treating sinusitis or allergic rhinitis according to the invention includes a central inner tube 1, a balloon 2 and a balloon catheter outer tube 3, all of which axially extend along a central axis A. In the axial direction, central inner tube 1 includes a distal end part 11 and a proximal end part 12; and in the radial direction, the distal end part 11 is surrounded by the balloon 2, and the proximal end part 12 is surrounded by the balloon catheter outer tube 3. The balloon catheter outer tube 3 is always radially spaced from the proximal end part 12, while one end of the balloon 2 is spaced from the distal end part 11, and the other end of the balloon 2 is connected to the distal end part 11. More specifically referring to FIG. 1, the first end 21 of the balloon 2 is connected to the distal end part 11 and the second end 22 is connected to one end of the balloon catheter outer tube 3, namely the second end 22 is radially spaced from the distal end part 11. The other end of the balloon catheter outer tube 3 opposite to the balloon 2 is connected to a balloon catheter receptacle (not shown). Accordingly, the balloon catheter outer tube 3 and the proximal end part 12 are always radially spaced from each other to define an expanding channel together, and the balloon 2 and the distal end part 11 define an expanding inner cavity together. The expanding channel and the expanding inner cavity are in communication with each other, and an expanding medium (such as gas or liquid) is pumped into the expanding inner cavity through the expanding channel so as to expand the wall of the balloon in the radial direction relative to the central axis A.

Figure 5:
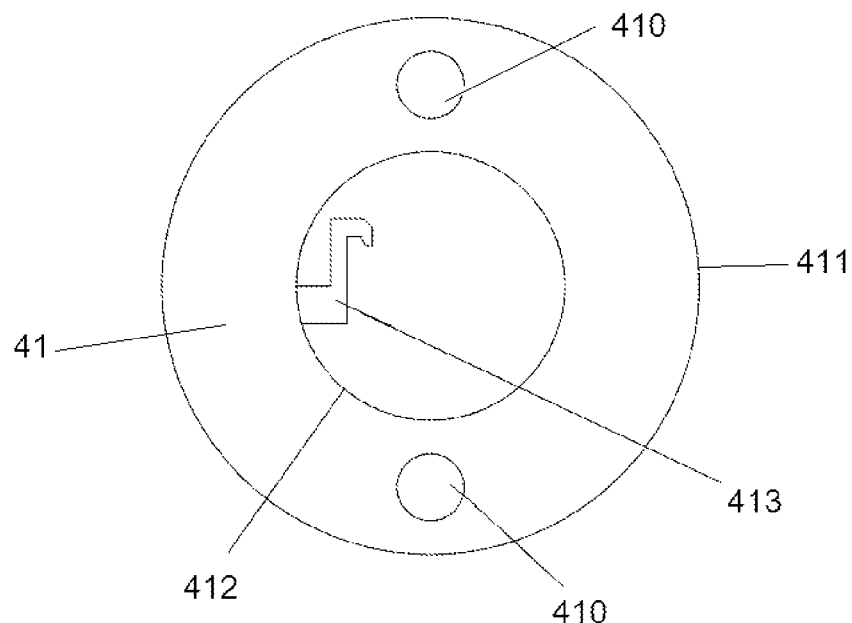
FIG. 5 is the side view of first grommet of the connector of the balloon system for treating sinusitis or allergic rhinitis according to one preferred embodiment of the invention.
Figure 6:
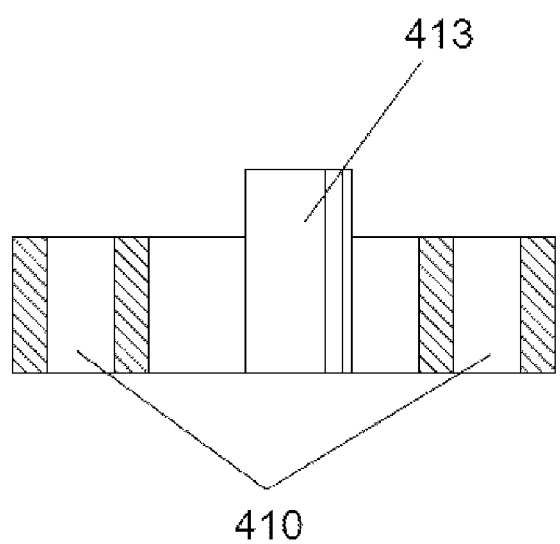
FIG. 6 is the section view of first grommet of the connector of the balloon system for treating sinusitis or allergic rhinitis according to one preferred embodiment of the invention.
Figure 7:
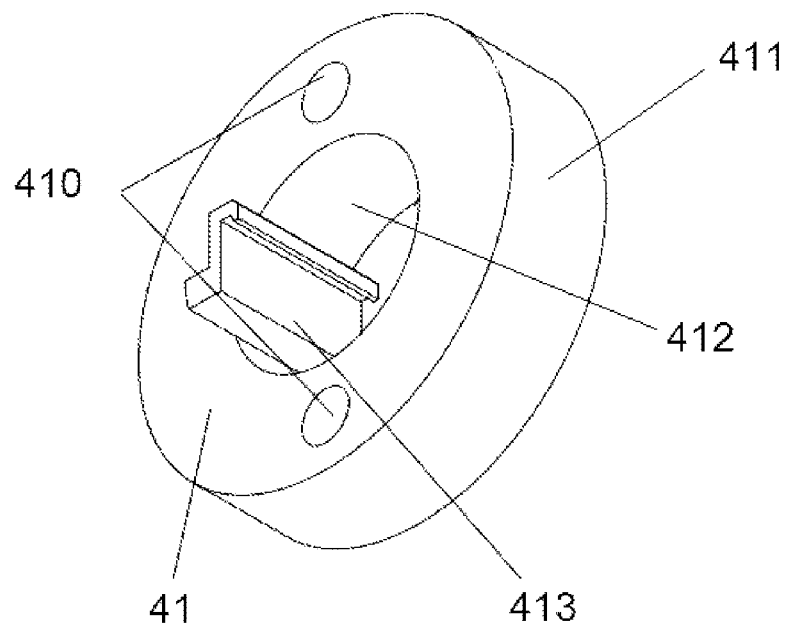
FIG. 7 is the perspective view of first grommet of the connector of the balloon system for treating sinusitis or allergic rhinitis according to one preferred embodiment of the invention.
Figure 8:
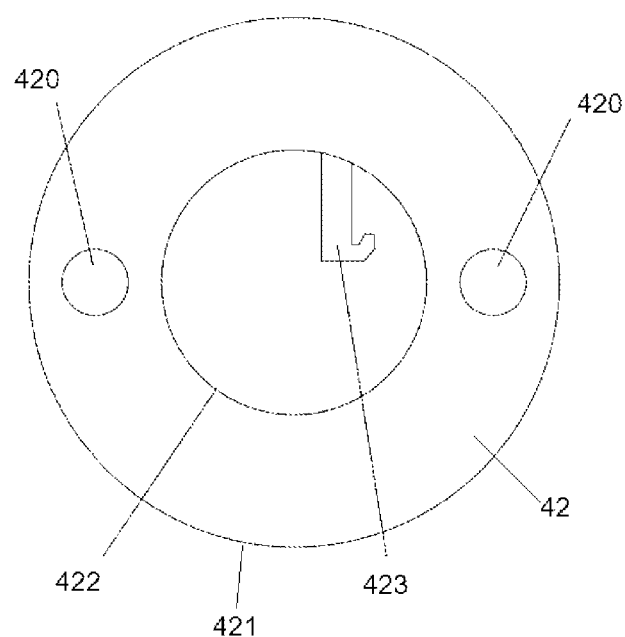
FIG. 8 is the side view of second grommet of the connector of the balloon system for treating sinusitis or allergic rhinitis according to one preferred embodiment of the invention.
Figure 9:
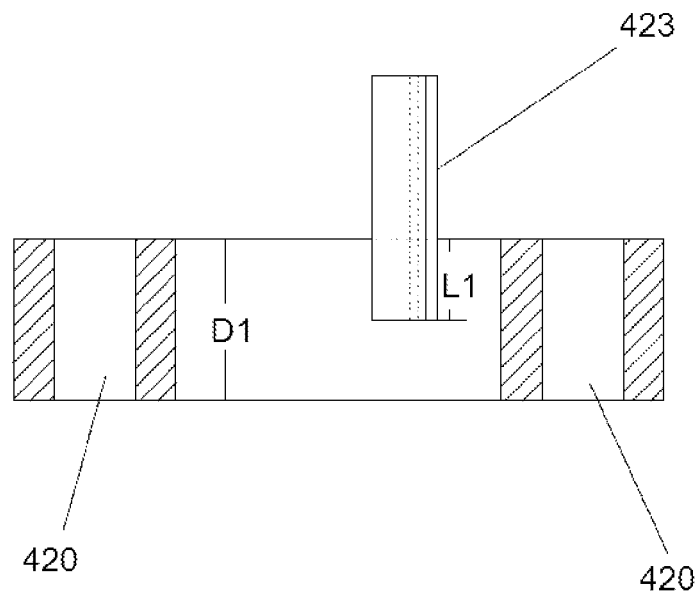
FIG. 9 is the section view of second grommet of the connector of the balloon system for treating sinusitis or allergic rhinitis according to one preferred embodiment of the invention.
Figure 10:
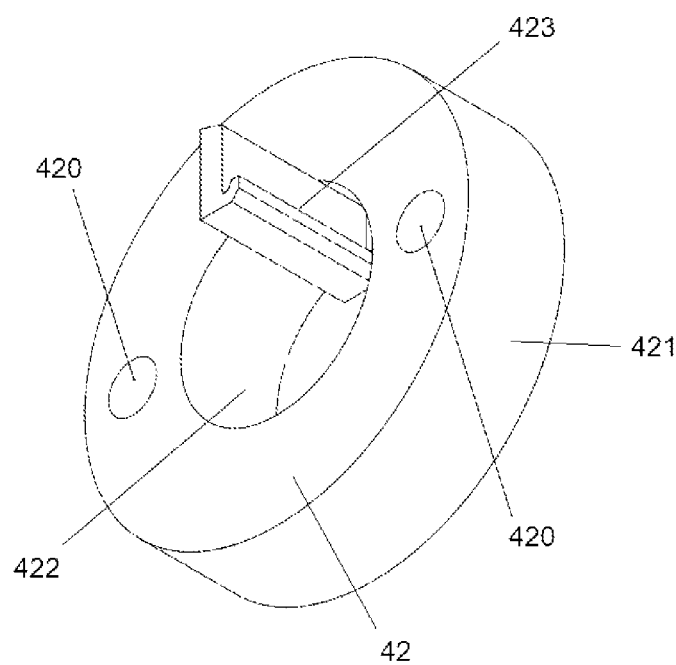
FIG. 10 is the perspective view of second grommet of the connector of the balloon system for treating sinusitis or allergic rhinitis according to one preferred embodiment of the invention.

As shown in FIG. 1 to FIG. 4, in the present embodiment, the distal end part 11 and the proximal end part 12 are connected by a connector 4, which also connects the second end 22 of the balloon 2 and the balloon catheter outer tube 3. The connector can be implemented by various means, and the following is an example but not to be limited. The connector includes a first grommet 41 and a second grommet 42, the first and second grommets 41, 42 can rotate coaxially and be relatively fixed with each other in axial direction, namely, both of them can rotate around the central axis A, but they are relatively fixed with each other in the direction of the central axis A, thus they cannot be separated in axial direction. As shown in FIG. 5 to FIG. 7, an outer edge 411 of the first grommet 41 and the second end 22 (see FIG. 1) of the balloon 2 are permanently connected (for example, by welding), and an inner edge 412 of the first grommet 41 and the distal end part 11 (see FIG. 1) of the central inner tube 1 are permanently connected (for example, by welding). As shown in FIG. 8 to FIG. 10, an outer edge 421 of the second grommet 42 and the balloon catheter outer tube 3 (see FIG. 1) are detachably connected (for example, by threaded connection), and an inner edge 422 of the second grommet 42 and the proximal end part 12 (see FIG. 1) of the central inner tube 1 are detachably connected (for example, by threaded connection).

As shown in FIG. 5 to FIG. 7, a first snap 413 disposed on the first grommet 41 projects radially inwardly from the inner edge 412 towards the central axis A, and axially from the first grommet 41 towards the second grommet 42. In the present embodiment, the first snap 413 is permanently connected with the first grommet 41 by welding. As shown in FIG. 8 to FIG. 10, a second snap 423 disposed on the second grommet 42 also projects radially inwardly from the inner edge 422 towards the central axis A, and axially from the second grommet 42 towards the first grommet 41. In the present embodiment, the second snap 423 is permanently connected with the second grommet 42 by welding.

Figure 11:
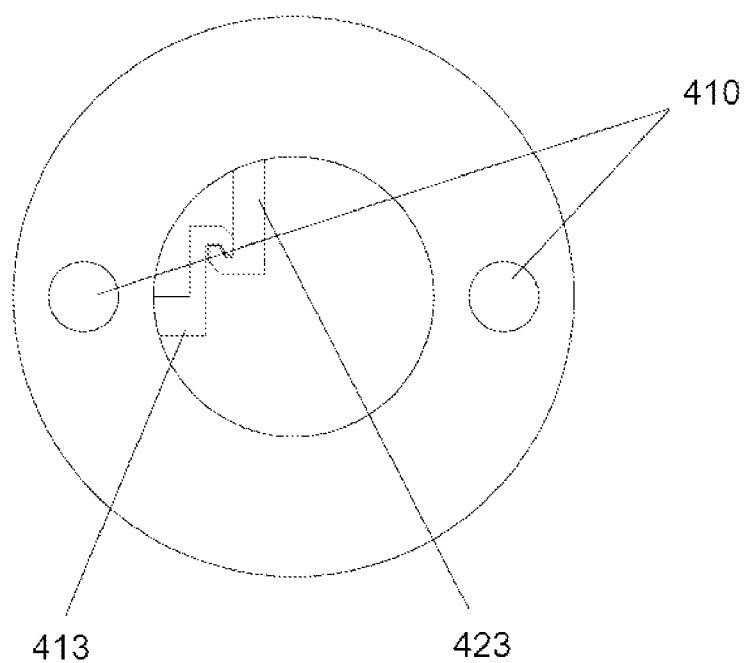
FIG. 11 is the side view of the connector of the balloon system for treating sinusitis or allergic rhinitis in matched status according to one preferred embodiment of the invention.
Figure 12:
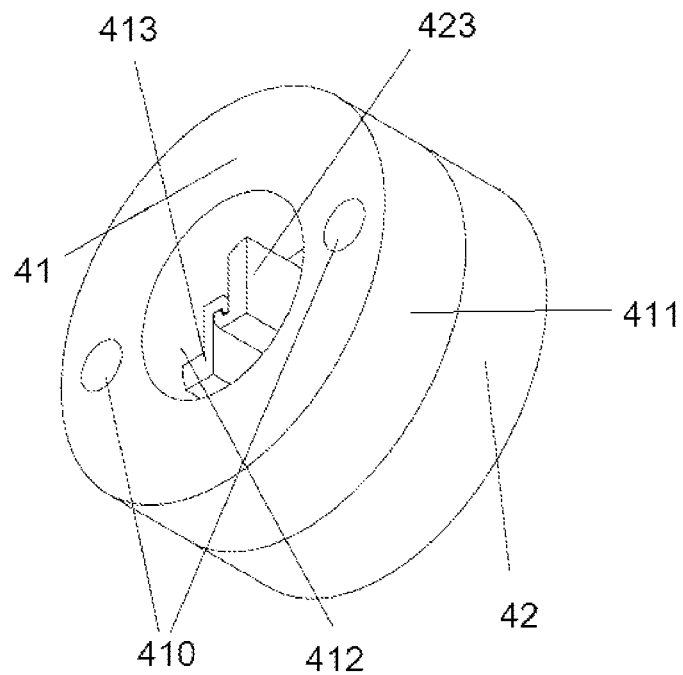
FIG. 12 is the perspective view of the connector of the balloon system for treating sinusitis or allergic rhinitis in matched status according to one preferred embodiment of the invention.
Figure 13:
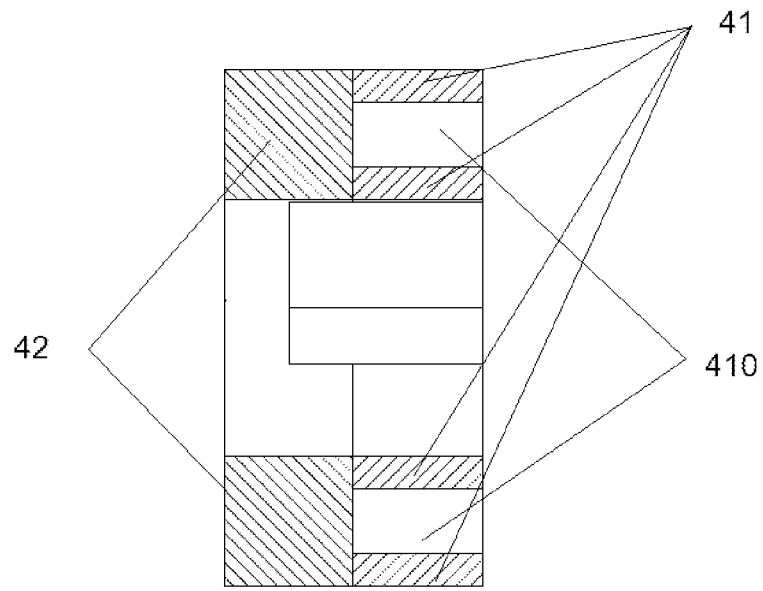
FIG. 13 is the section view of the connector of the balloon system for treating sinusitis or allergic rhinitis in matched status according to one preferred embodiment of the invention.

By the means of the first grommet 41 and the second grommet 42 rotating around the axis A, the first snap 413 can be matched and connected with the second snap 423. Referring to FIG. 11 to FIG. 13, the projecting part of the first snap 413 from the first grommet 41 and the projecting part of the second snap 423 from the second grommet 42 limit and fix each other.

Figure 14:
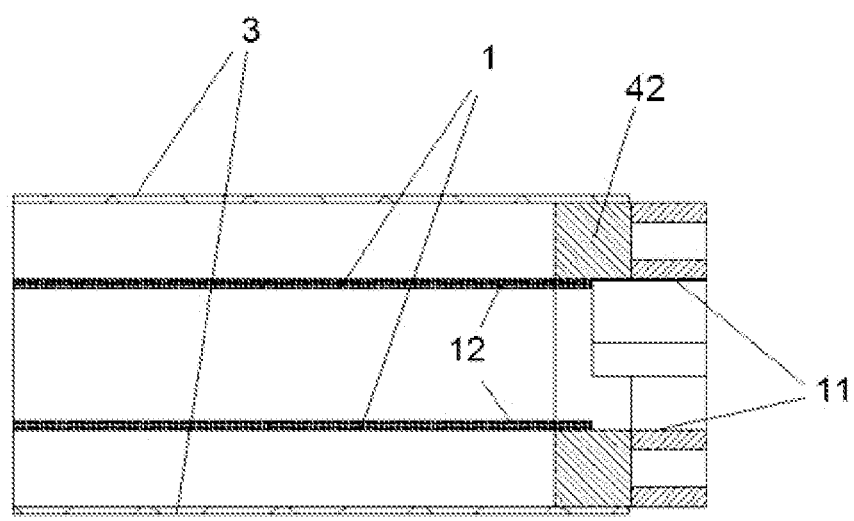
FIG. 14 is the partial section view of the balloon system for treating sinusitis or allergic rhinitis with the connector in matched status according to one preferred embodiment of the invention.

In one preferred embodiment of the present invention, the axial extending length L1 of the second snap 423 inside the second grommet 42 is smaller than the thickness D1 of the second grommet 42, and the preferred ratio of L1/D1 equals to ⅓ to ¾. As shown in FIG. 9, a thread connection with the proximal end part 12 of central inner tube 1 (see FIG. 14) is disposed on the remaining axial length (D1-L1) of the inner edge 422 of the second grommet 42.

As shown in FIG. 3 to FIG. 13, the first grommet 41 has at least one axially throughout first gas port 410, and the second grommet 42 also has at least one axially throughout second gas port 420. When the first snap 413 and the second snap 423 match and limit each other, the first gas port 410 and the second gas port 420 are completely misaligned with each other, but when the first snap 413 and the second snap 423 don't match and limit each other, the first gas port 410 and the second gas port 420 are at least partially communicated with each other.

Figure 15:
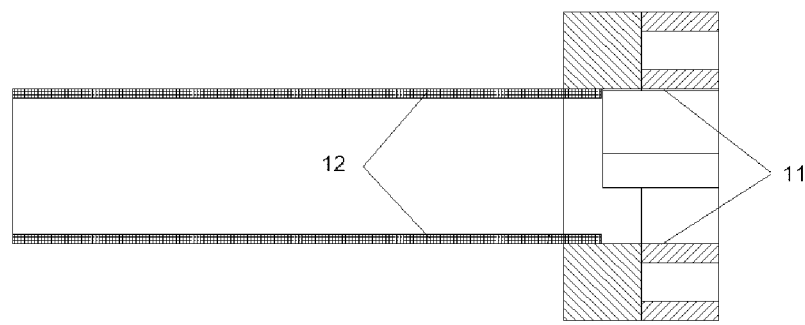
FIG. 15 is the partial section view of the balloon system for treating sinusitis or allergic rhinitis with the connector in matched status after the balloon catheter outer tube and the balloon disconnected from each other according to one preferred embodiment of the invention.
Figure 16:
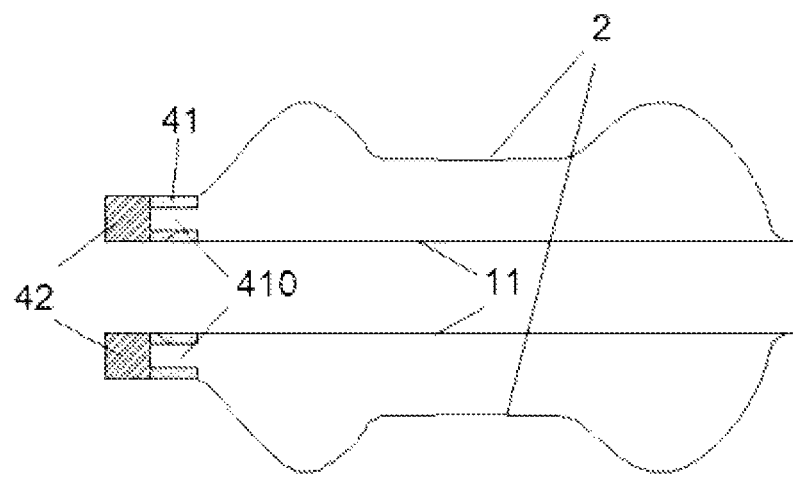
FIG. 16 is the partial section view of the balloon system for treating sinusitis or allergic rhinitis with the connector in matched status after the proximal end part and the distal end part disconnected from each other according to one preferred embodiment of the invention.

In the present embodiment, the first and second gas ports are shown as symmetrical with each other. In unmatched state, the first gas port 410 and the second gas port 420 are completely aligned with each other, the expanding channel and the expanding inner cavity are communicated, and the expanding medium (such as gas or liquid) is pumped into the expanding inner cavity through the expanding channel so as to expand the wall of the balloon in radial direction relative to the central axis A. After the balloon 2 reaches an appropriately filled state, the central inner tube 1 is rotated around the central axis A, and the second grommet 42 can rotate around the central axis A under the effect of frictional force, causing the second snap 423 and the first snap 413 to match and limit each other, and place the connector 4 in interlocked status (refer to FIG. 14). Meanwhile the first gas port 410 and the second gas port 420 are completely misaligned with each other, and the expanding channel and the expanding inner cavity are uncommunicated. The expanding medium is sealed inside the expanding inner cavity to maintain the filled state of the expanding inner cavity. After interlocked status, the balloon catheter outer tube 3 is rotated around the central axis A and disconnected from the outer edge 421 of the second grommet 42, causing the balloon catheter outer tube 3 and the balloon 2 to be disconnected from each other. The partial section view after disconnection is shown in FIG. 15. Next, the central inner tube 1 is rotated around the central axis A again, the proximal end part 12 is disconnected from the inner edge 422 of the second grommet 42, causing the proximal end part 12 and the distal end part 11 to be disconnected from each other The partial section view after disconnection is shown in FIG. 16.

According to above description, the balloon system for treating sinusitis or allergic rhinitis of the invention can be used to deliver the medicine according to the prescribed dosage during and/or after minimally invasive surgery, and also can be used after sinus atherectomy or used directly without sinus atherectomy. The filled balloon remains in the diseased region of the patient for short-term or long-term temporal support.

The balloon 2 may be a compliant balloon or half-compliant balloon, which is preferably folded as a minimal outer profile before coming into the nasal cavity, so as to go through the gap of the nasal cavity and reach the diseased region. The filled balloon may have a cylindrical shape, and further may have a dumb-bell shape or a bi-conical shape after expansion, preferably a dumb-bell shape. Both ends of the balloon have a larger diameter for remaining in the nasal cavity after expansion, thus the position of the balloon will not change freely in short-term or long-term after implantation. Preferably, the filled balloon 2 has a diameter of 2 mm to 30 mm and a length of 5 mm to 60 mm, and the folded balloon 2 has an outer diameter of 0.5 mm to 5 mm.

The balloon 2 of the balloon system for treating sinusitis or allergic rhinitis of the invention can be made of degradable materials or non-degradable materials. The non-degradable balloon can be removed in 15 to 30 days after implantation, and the degradable balloon will be degraded and absorbed as time goes on, with the preferred degradation period being 15 days to 9 months. The materials of the balloon include but are not limited to non-degradable materials such as polyamide, polyamide-polyether block copolymer, polytetrafluoroethylene, polyurethane, vinylsiloxane rubber, natural rubber, butadiene-acrylonitrile rubber; degradable materials, such as polylactic acid, L-polylactic acid, polyglycolic acid/ polylactic acid copolymer, polycaprolactone, polyhydroxybutyratehydroxyvalerate, polyacetylglutamic acid, polyorthodester, polyoxyethylene/polybutylene copolymer and so on.

Figure 17:
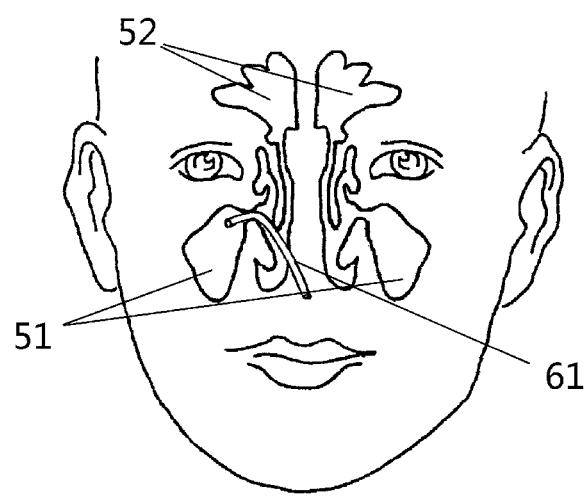
FIG. 17 shows the balloon system for treating sinusitis or allergic rhinitis according to another preferred embodiment of the invention, wherein the distal end part of the balloon system is replaced with an implanted flexible tube for providing medicine in long-term.

Furthermore, after complete degradation of the materials of the balloon, the distal end part 11 made of non-degradable or slowly degradable polymer materials will remain in the nasal sinus ostium for support, and the distal end part 11 can be taken out or remain in the nasal sinus ostium. If it remains in the nasal sinus ostium, the patient himself can connect any suitable spray device with the distal end part 11 to deliver medicine into the nasal sinus if needed. Of course, a more convenient method is using a longer flexible tube 61 with certain strength instead of the distal end part 11. For example, the material of the flexible tube 61 can be a polymer with shore hardness of 35 D to 80 D. Thus the flexible tube may extend enough up to the muzzle, which is more convenient for the patient to spray medicine himself, as shown in FIG. 17. In FIG. 17, maxillary sinus is indicated by 51, frontal sinus is indicated by 52, and the implanted flexible tube for providing medicine in long-term is indicated by 61.

Furthermore, the expanding medium (such as gas or liquid) in the present invention includes medicine molecules that can slowly permeate into the diseased region through the wall of the balloon. Obviously, if the material of the balloon 2 is degradable, the medicine molecules in the expanding medium will permeate as the balloon degrades.

Furthermore, the materials of the balloon 2 may be a mixture of two or more polymers, one or more of which is fast-degradable or water-soluble polymer. These kinds of materials (fast-degradable or water-soluble polymer) may be softened or dissolved in one or several days. When the balloon expands the nasal sinus tissue, the inside of the balloon is full filled with medicine liquid. As the fast-degradable or water-soluble polymer is continually dissolved out from the balloon materials, the medicine liquid in the balloon will gradually permeate into the diseased region through the wall of the balloon. The medicine may be same with the medicine applied on the surface of the balloon, or different from that for later stage of treatment. After medicine permeation is finished, the rest part of the balloon can be taken out from the nasal cavity. The key of the solution is that the inner tube of the balloon must be made of materials with relatively better rigidity, such that the balloon will not be crashed even if the supporting pressure for the balloon disappears. Typical water-soluble polymers include polyethylene glycol (PEG), polyethylene glycol block copolymer (such as PEG/PLGA, PEG/PLA bi-block or tri-block copolymer, or PEG/PLGA, PEG/PLA bi-block or tri-block random copolymer or alternating copolymer, which includes polyethylene glycol as the end of macromolecular chain), sucrose, starch, sodium alginate, polyvinylpyrrolidone (PVP), polyvinyl alcohol (PVA) and so on.

Furthermore, the outer surface of the balloon 2 of the balloon system for treating sinusitis or allergic rhinitis of the invention can include a medicine sustained release coating, and the coating with pre-prepared medicine liquid may be applied on the outer surface of the balloon 2 by dipping, painting, spraying, sputtering and so on. After implantation, the medicine inside the coating on the surface of the balloon releases continually for treating the diseased region around. According to the balloon implantation time and disease requirement, the medicine release time may be controlled in 7 days to 6 months. When the expanding medium of the balloon includes medicine molecules which gradually release and permeate as the degradation of the wall of the balloon, this treatment is typically carried out after the effect of the medicine sustained release coating, referred as the second time (later stage) of medicine releasing. That is to say, besides the coating (first slow release medicine in solid form), the balloon system of the invention further include the expanding medium (second slow release medicine in liquid/gas form) inside the balloon for later stage of treatment.

In above medicine coating, available medicine includes but not limited to the following medicines and their composition and/or mixture: long-acting sterol hormone, anti-inflammatory drug, anti-allergic reaction drug, parasympathicolytic drug, anti-histamine drug, anti-infectious drug, anti-platelet drug, anti-coagulant drug, anti-thrombotic drug, anti-scar drug, anti-hyperplasia drug, chemotherapeutic drug, anti-neoplastic drug, decongestant, healing accelerator, vitamin (such as retinoic acid, vitamin A, vitamin B, and their derivatives), immunomodulating agent, immunosuppressive drug.

Obviously, many modifications and variations of the present invention are possible in light of the above teachings and may be practiced otherwise than as specifically described while within the scope of the appended claims.

What is claimed is:

1. The balloon system for treating sinusitis or allergic rhinitis comprising:
   a central inner tube (1), a balloon (2) to be filled and a balloon catheter outer tube (3), all of which axially extend;
   the central inner tube (1) including a distal end part (11) and a proximal end part (12) in axial direction;
   a first end (21) of the balloon (2) being connected to the distal end part (11);
   the balloon catheter outer tube (3) being radially outwardly spaced from the proximal end part (12);
   a connector (4) configured to detachably connect the distal end part (11) and the proximal end part (12) with each other;
   the connector further configured to detachably connect a second end (22) of the balloon (2) and the balloon catheter outer tube (3) with each other;
   the connector (4) including a first grommet (41) and a second grommet (42) rotating coaxially and relatively fixed with each other in axial direction;
   each of the first grommet (41) and second grommet (42) having at least one gas port (410, 420);
   wherein an outer edge (411) of the first grommet (41) and the balloon (2) are permanently connected;
   wherein an outer edge (421) of the second grommet (42) and the balloon catheter outer tube (3) are detachably connected;
   wherein an inner edge (412) of the first grommet (41) and the distal end part (11) are permanently connected;
   wherein an inner edge (422) of the second grommet (42) and the proximal end part (12) are detachably connected; and a first snap (413) is disposed on the first grommet (41), and a second snap (423) is disposed on the second grommet (42) and interlocked with the first snap (413).

2. The balloon system for treating sinusitis or allergic rhinitis according to claim 1, wherein the unfilled balloon (2) has a radial diameter and axial lengths of 0.5 mm to 5 mm, and the filled balloon (2) has a radial diameter of 2 mm to 30 mm and a axial length of 5 mm to 60 mm.

3. The balloon system for treating sinusitis or allergic rhinitis according to claim 2, wherein the filled balloon (2) has a cylindrical shape, a dumb-bell shape or a bi-conical shape.

4. The balloon system for treating sinusitis or allergic rhinitis according to claim 1, wherein the balloon (2) is made of degradable materials or non-degradable materials.

5. The balloon system for treating sinusitis or allergic rhinitis according to claim 4, wherein the balloon (2) made of non-degradable materials is removed in 15 to 30 days after implantation.

6. The balloon system for treating sinusitis or allergic rhinitis according to claim 4, wherein the degradation period of the balloon (2) made of degradable materials is 15 days to 9 months.

7. The balloon system for treating sinusitis or allergic rhinitis according to claim 1, wherein the balloon (2) is made of copolymers including water-soluble materials.

8. The balloon system for treating sinusitis or allergic rhinitis according to claim 1, wherein an outer surface of the balloon (2) includes a medicine sustained release coating.

9. The balloon system for treating sinusitis or allergic rhinitis according to claim 8, wherein a medicine release time of the medicine sustained release coating is 7 days to 6 months.

10. The balloon system for treating sinusitis or allergic rhinitis according to claim 1, wherein the balloon (2) and the distal end part (11) define an expanding inner cavity for containing an expanding medium which includes medicine molecules.

11. A balloon system for treating sinusitis or allergic rhinitis, comprising:
- a central inner tube (1), a balloon (2) to be filled and a balloon catheter outer tube (3), all of which axially extend;
- the central inner tube (1) including a distal end part (11) and a proximal end part (12) in axial direction;
- a first end (21) of the balloon (2) being connected to the distal end part (11);
- the balloon catheter outer tube (3) being radially outwardly spaced from the proximal end part (12);
- a connector (4) configured to detachably connect the distal end part (11) and the proximal end part (12) with each other;
- the connector further configured to detachably connect a second end (22) of the balloon (2) and the balloon catheter outer tube (3) with each other;
- the connector (4) including a first grommet (41) and a second grommet (42) rotating coaxially and relatively fixed with each other in axial direction;
- each of the first grommet (41) and second grommet (42) having at least one gas port (410, 420); and
- wherein when a first snap (413) is interlocked with a second snap (423), the at least one first gas port (410) of the first grommet (41) and the at least one gas port (420) of the second grommet (42) are completely misaligned with each other.

12. The balloon system for treating sinusitis or allergic rhinitis according to claim 11, wherein the unfilled balloon (2) has a radial diameter and axial lengths of 0.5 mm to 5 mm, and the filled balloon (2) has a radial diameter of 2 mm to 30 mm and a axial length of 5 mm to 60 mm.

13. The balloon system for treating sinusitis or allergic rhinitis according to claim 12, wherein the filled balloon (2) has a cylindrical shape, a dumb-bell shape or a bi-conical shape.

14. The balloon system for treating sinusitis or allergic rhinitis according to claim 11, wherein the balloon (2) is made of degradable materials or non-degradable materials.

15. The balloon system for treating sinusitis or allergic rhinitis according to claim 14, wherein the balloon (2) made of non-degradable materials is removed in 15 to 30 days after implantation.

16. The balloon system for treating sinusitis or allergic rhinitis according to claim 14, wherein the degradation period of the balloon (2) made of degradable materials is 15 days to 9 months.

17. The balloon system for treating sinusitis or allergic rhinitis according to claim 11, wherein the balloon (2) is made of copolymers including water-soluble materials.

18. The balloon system for treating sinusitis or allergic rhinitis according to claim 11, wherein an outer surface of the balloon (2) includes a medicine sustained release coating.

19. The balloon system for treating sinusitis or allergic rhinitis according to claim 18, wherein a medicine release time of the medicine sustained release coating is 7 days to 6 months.

20. The balloon system for treating sinusitis or allergic rhinitis according to claim 11, wherein the balloon (2) and the distal end part (11) define an expanding inner cavity for containing an expanding medium which includes medicine molecules.

\* \* \* \* \*